US008377380B2

(12) United States Patent
Yorita et al.

(10) Patent No.: US 8,377,380 B2
(45) Date of Patent: Feb. 19, 2013

(54) SENSING DEVICE

(75) Inventors: Tomoya Yorita, Sayama (JP); Shunichi Wakamatsu, Sayama (JP); Shigenori Watanabe, Sayama (JP); Takeru Mutoh, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 110 days.

(21) Appl. No.: 12/803,228

(22) Filed: Jun. 22, 2010

(65) Prior Publication Data
US 2010/0329928 A1 Dec. 30, 2010

(30) Foreign Application Priority Data

Jun. 30, 2009 (JP) ................................. 2009-156185

(51) Int. Cl.
*G01N 27/00* (2006.01)
(52) U.S. Cl. .... 422/82.01; 422/504; 422/73; 422/82.05; 422/82.08; 422/82.09; 422/82.11; 422/407; 422/501; 422/502; 422/503; 714/752; 436/164; 436/177; 436/43; 436/63; 506/30; 435/29; 435/4; 435/7.1; 250/214.1; 250/251; 250/576; 530/408
(58) Field of Classification Search ............... 422/73, 422/82.05, 82.09, 82.11, 502, 503, 504, 82.01, 422/82.08, 407, 501; 436/164, 177, 43, 63; 506/30; 435/29, 4, 6, 7.1; 250/214.1, 251, 250/576; 530/408; 714/752
See application file for complete search history.

(56) References Cited

FOREIGN PATENT DOCUMENTS

| EP | 2058642 A1 * | 5/2009 |
| JP | 1-208004 | 8/1989 |
| JP | 6-273304 | 9/1994 |
| JP | 8-288789 | 11/1996 |
| JP | 11-183479 | 7/1999 |
| JP | 2004-245613 | 9/2004 |
| JP | 2005-331445 | 12/2005 |
| JP | 2006-030167 | 2/2006 |
| JP | 2006-194867 | 7/2006 |
| JP | 2006-220606 | 8/2006 |
| JP | 2006-250926 | 9/2006 |
| JP | 2007-040717 | 2/2007 |

(Continued)

*Primary Examiner* — Dennis M White
(74) *Attorney, Agent, or Firm* — Jordan and Hamburg LLP

(57) ABSTRACT

To provide a sensing device using a piezoelectric sensor having an oscillation area for detection and an oscillation area for reference and capable of achieving a high measurement sensitivity by improving shapes of excitation electrodes. On a quartz-crystal piece 20a, there are provided strip-shaped left side area and right side area which are formed symmetrically to be separated from each other into left and right with respect to a center of a circle 53 being a contour of a planar shape of a reaction channel 52 and extend in a longitudinal direction in a parallel manner. Each of the areas is set to have a size in which both corner portions 100 on the left side of the left side area and both corner portions 100 on the right side of the right side area protrude to the outside of the circle 53, the corner portions 100 that protrude to the outside are cut to make the left side area and the right side area position inside of the circle 53, and an excitation electrode 21a for measurement and an excitation electrode 21b for reference are respectively formed on the right side area and the left side area.

3 Claims, 12 Drawing Sheets

FOREIGN PATENT DOCUMENTS

| | | |
|---|---|---|
| JP | 2007-054817 | 3/2007 |
| JP | 2007-108170 | 4/2007 |
| JP | 2008-058086 | 3/2008 |
| JP | 2008-102118 | 5/2008 |
| JP | 2008-107167 | 5/2008 |
| JP | 2008-203003 | 9/2008 |
| JP | 2009-135830 | 6/2009 |
| JP | 2010-002413 | 1/2010 |
| JP | 2010-004388 | 1/2010 |
| JP | 2010-101852 | 5/2010 |
| JP | 2010-123856 | 6/2010 |
| JP | 2011-022139 | 2/2011 |

* cited by examiner (a)

(b)

SENSING DEVICE

BACKGROUND OF THE INVENTION

1. Field of the Invention

The present invention relates to a sensing device for sensing a substance to be sensed contained in a sample solution based on a natural frequency of a piezoelectric resonator such as a quartz-crystal resonator.

2. Description of the Related Art

As a sensing device for sensing and measuring a trace substance contained in a sample solution, there has been known one which uses a quartz-crystal sensor. As this type of sensing device, one that detects a substance to be sensed while letting a sample solution flow, as disclosed in Patent Document 1, has been known. A quartz-crystal piece 10 of a quartz-crystal sensor of the sensing device is placed on a wiring board 13 so as to block a hole portion 13a of the wiring board 13 as shown in FIG. 11, and is pressed by a quartz-crystal pressing member 14 when an annular pressing portion 14a of the member abuts thereon. Further, in a state where the quartz-crystal sensor is mounted on a bottom portion of a case 16, a reaction channel 17 is formed to surround an area facing a front surface of the quartz-crystal sensor, and at this time, a substance to be sensed in a sample solution is absorbed in an absorption layer 12 on the quartz-crystal piece 10. A buffer solution is flowed through the reaction channel 17 before letting the sample solution flow through the channel, and by measuring a variation in frequency in the quartz-crystal piece 10 at this time, a concentration of the substance to be sensed in the sample solution is measured.

Meanwhile, the present inventor has been studying a quartz-crystal sensor of twin sensor type. This quartz-crystal sensor includes two excitation electrodes (a detection electrode and a reference electrode) on one surface side of a quartz-crystal piece to reduce an influence of an external factor of measurement environment such as a temperature, for instance, in which an absorption layer formed of a biological substance or the like is formed on a front surface of the detection electrode. Note that by corresponding to the excitation electrodes, excitation electrodes are provided also on a rear surface side of the quartz-crystal piece, thereby forming an oscillation area for detection and an oscillation area for reference. Accordingly, since only the detection electrode is affected by a mass change caused by an absorption of a substance to be sensed, by subtracting an oscillation frequency taken out from the reference electrode from an oscillation frequency taken out from the detection electrode, it is possible to obtain a highly accurate measured result from which the external factor is removed.

Meanwhile, when the measurement is conducted under a liquid phase atmosphere, a sensitivity of quartz-crystal sensor is deteriorated due to a viscosity of a liquid. Accordingly, in order to improve the sensitivity, it is desirable that the detection electrode and the reference electrode are designed to be large in size.

However, since the detection electrode is affected by an oscillation energy from the reference electrode, in order to reduce an influence of noise due to the oscillation on the detection result, it is preferable to increase a space between these electrodes. To ensure the space, the size of each of the electrodes has to be reduced, which also reduces a forming area of the absorption layer, resulting in a problem that the measurement sensitivity is deteriorated.

[Patent Document 1] Japanese Patent Application Laid-open No. 2008-58086 (paragraph [0014], FIG. 11 and FIG. 13)

SUMMARY OF THE INVENTION

The present invention has been made based on such circumstances, and an object thereof is to provide a sensing device using a piezoelectric sensor having an oscillation area for detection and an oscillation area for reference and capable of achieving a high measurement sensitivity by improving shapes of excitation electrodes.

A sensing device of the present invention being a device that has a piezoelectric resonator having a piezoelectric piece on which two pairs of excitation electrodes are provided to form an oscillation area for measurement and an oscillation area for reference, the areas being separated from each other, in which an absorption layer absorbing a substance to be sensed in a sample fluid is formed on one excitation electrode positioned on one surface side of the piezoelectric piece of the electrode pair forming the oscillation area for measurement, and senses, by making the absorption layer absorb the substance to be sensed in the sample fluid and supplying the sample fluid also onto the oscillation area for reference on the one surface side of the piezoelectric piece, the substance to be sensed based on an oscillation frequency of the oscillation area for measurement and an oscillation frequency of the oscillation area for reference, the sensing device includes: a surrounding member provided, to form a sample fluid supply space common to the oscillation area for measurement and the oscillation area for reference, on one surface side of the piezoelectric resonator to be positioned outside of the excitation electrodes that form the oscillation areas and to surround the excitation electrodes in a circular manner; and a holding member holding an outside of the oscillation area for measurement and the oscillation area for reference on the other surface side of the piezoelectric resonator, in which the excitation electrodes are formed in the following shapes: a. the excitation electrodes are formed symmetrically to be separated from each other into left and right with respect to a center of a circle being a contour of a planar shape of the sample fluid supply space to form strip-shaped left side area and right side area extending in a longitudinal direction in a parallel manner, b. each of both corner portions on the left side of the left side area and both corner portions on the right side of the right side area is set to have a size to protrude to the outside of the circle, and c. the corner portions that protrude to the outside are cut to make the left side area and the right side area position inside of the circle, and the excitation electrode of the oscillation area for reference and the excitation electrode of the oscillation area for measurement are respectively formed on the left side area and the right side area.

Further, the sensing device may take structures as follows.

1. A structure in which one end sides of both the excitation electrodes provided on the one surface side of the piezoelectric resonator are mutually connected by an electrode within the circular sample fluid supply space to provide a common potential to the excitation electrodes, and both the excitation electrodes provided on the other surface side of the piezoelectric resonator are electrically separated from each other.

2. A structure in which a supply channel supplying a sample fluid and a discharge channel discharging the sample fluid are connected to the sample fluid supply space, and the measurement of oscillation frequency of a piezoelectric sensor is performed while letting the sample fluid flow into the sample fluid supply space.

According to the present invention, strip-shaped excitation electrodes formed on one surface side of a piezoelectric piece are formed by cutting portions of corner portions, being lateral portions of the excitation electrodes, protruding from a circular area surrounded by a surrounding member. Therefore, it is possible to enlarge areas of the excitation electrodes within an area being surrounded by the surrounding member and including oscillation areas of the piezoelectric sensor, which contributes to improve a measurement sensitivity.

DETAILED DESCRIPTION OF THE PREFERRED EMBODIMENT(S)

Although a sensing device according to an embodiment of the present invention has a characteristic in shapes of excitation electrodes of a piezoelectric sensor, an entire structure of the sensing device will be briefly described. As shown in later-described FIG. 8, the sensing device includes: a sensor unit 2 on which a piezoelectric sensor is mounted; a supply system supplying a liquid to the sensor unit 2; a discharge system discharging the liquid from the sensor unit 2; an oscillator circuit unit 30; a measurement circuit part 81; and a data processing part 82.

Figure 1:
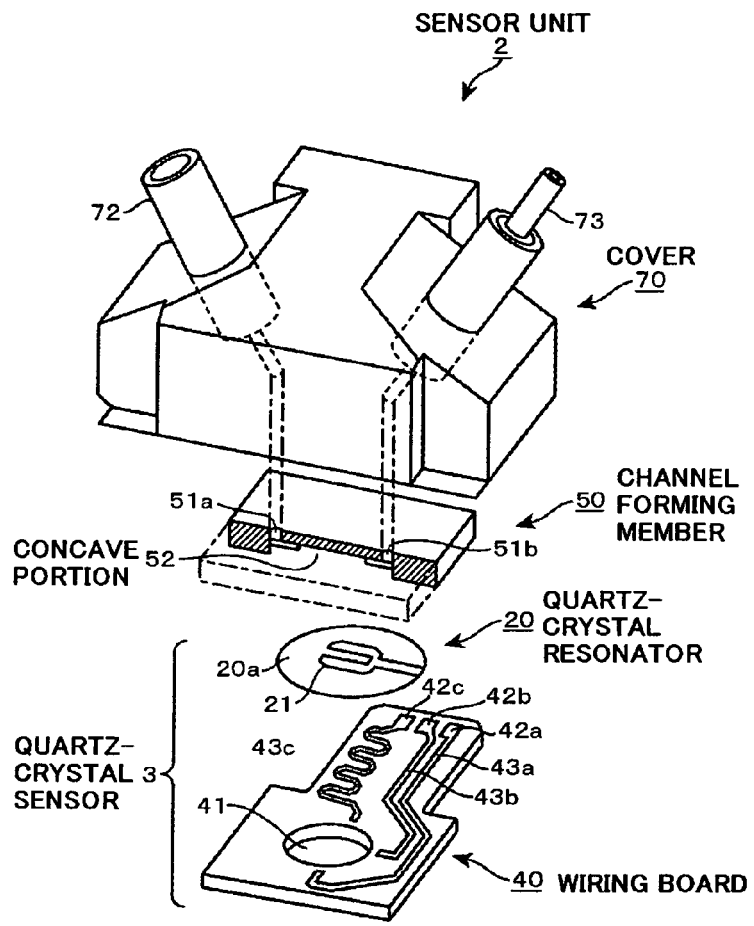
FIG. 1 is an exploded perspective view showing a sensor unit being a part of a sensing device according to the present invention.
Figure 1:
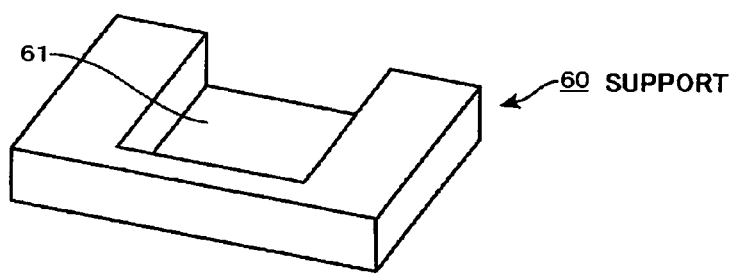

First, a quartz-crystal sensor being a piezoelectric sensor will be described with reference to FIG. 1. A quartz-crystal sensor 3 includes a quartz-crystal resonator 20 being a piezoelectric resonator and a wiring board 40. As shown in FIG. 1 and FIG. 3(a), the quartz-crystal resonator 20 includes, for instance, a circular quartz-crystal piece 20a being a piezoelectric piece, in which an electrode having a shape close to that of claws is formed on a front surface of the quartz-crystal piece 20a. The electrode is formed of two excitation electrodes 21a, 21b disposed in parallel to be separated from each other, a coupling portion 27 coupling one end sides of these excitation electrodes 21a, 21b, and a lead-out electrode 28 linearly extending from a center portion of the coupling portion 27 to a circumferential edge of the quartz-crystal piece 20a. One excitation electrode 21a forms, on the quartz-crystal piece 20a, an oscillation area for detection together with a later-described electrode 22a on a rear surface side. The other excitation electrode 21b is for forming, on the quartz-crystal piece 20a, an oscillation area for reference together with a later-described electrode 22b on the rear surface side. Therefore, it can be said that the coupling portion 27 forms a part of the lead-out electrode 28.

Figure 5:
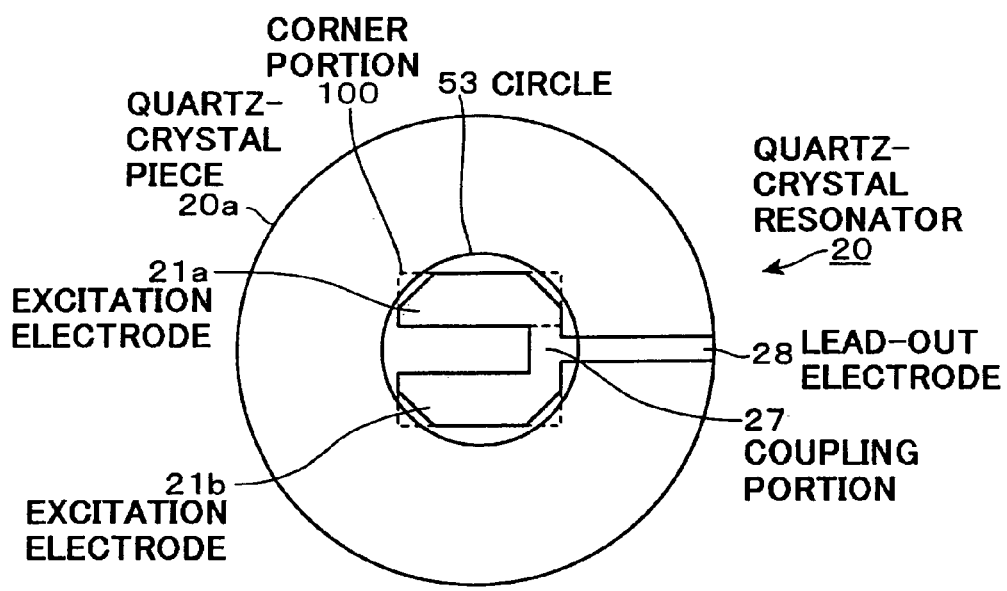
FIG. 5 is an explanatory diagram showing a positional relationship when the channel forming member and the quartz-crystal resonator abut.
Figure 6:
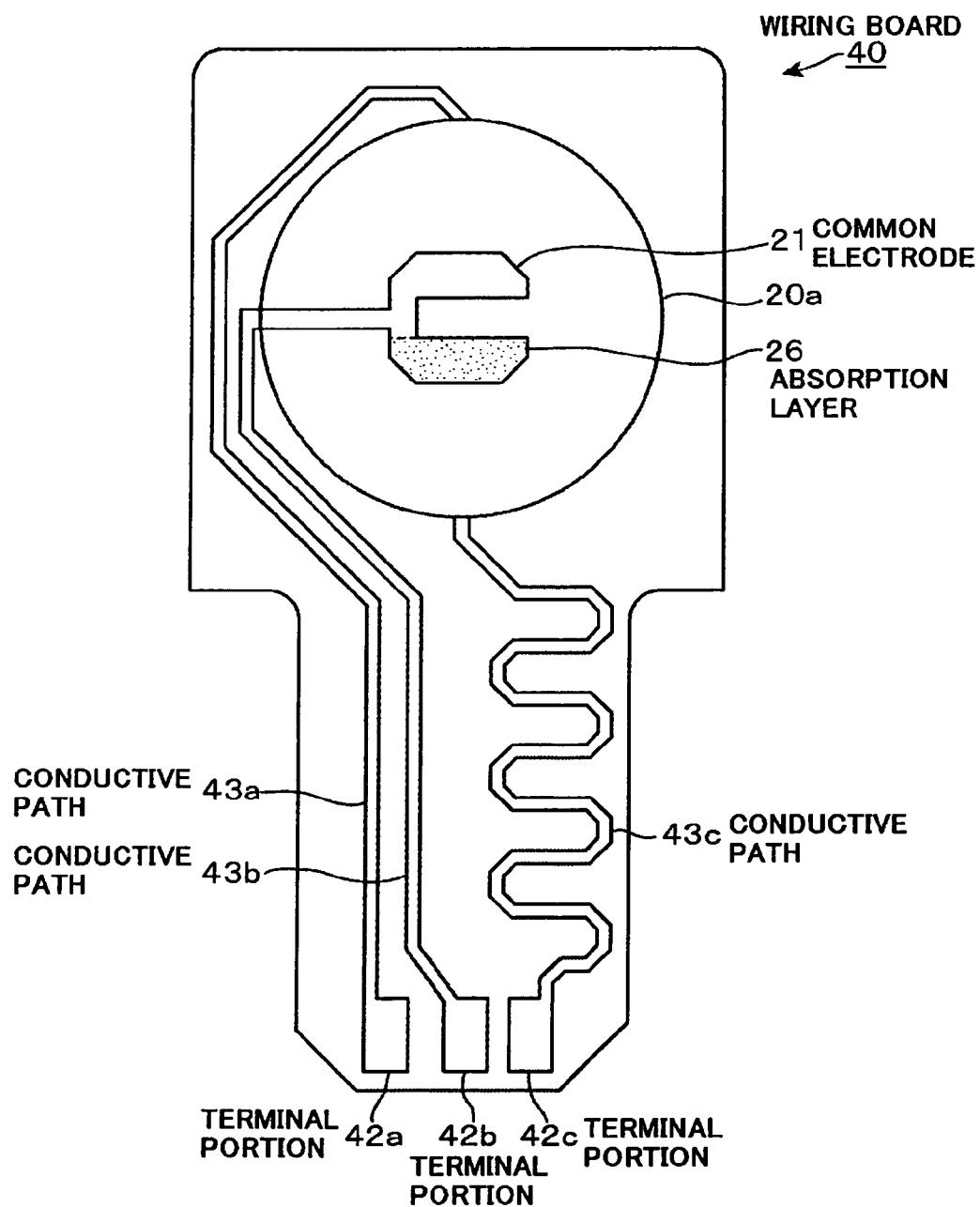
FIG. 6 is a plan view showing the quartz-crystal sensor.

Here, shapes of the excitation electrodes 21a, 21b will be described in detail. The quartz-crystal resonator 20 is surrounded by a contour of an outer periphery (circumferential edge) of a concave portion 52 of a channel forming member 50 being a later-described surrounding member, and the excitation electrodes 21a, 21b have to be positioned inside of the concave portion 52. The reason thereof is, although being described also in the item of "BACKGROUND OF THE INVENTION", that when the excitation electrodes 21a, 21b are positioned outside of the concave portion 52, they are trodden, namely, pressed by the channel forming member 50, and in such a case, the oscillation becomes unstable. Therefore, strip-shaped corner portions 100 are cut to form a flat hexagonal shape, as shown in FIG. 5.

The shape of the electrode will be further described in detail with reference to FIG. 5. Since the contour of the outer periphery of the concave portion 52 is a circular shape, the contour is referred to as "circle" and is denoted by a reference numeral 53 in the explanation here. First, there are formed a left side area (area on the lower side in FIG. 5) and a right side area (area on the upper side in FIG. 5) being two strip-shaped areas disposed symmetrically to be separated into left and right (above and below in FIG. 5) with respect to a center of the circle 53 and extending in a longitudinal direction (horizontal direction in FIG. 5) in a parallel manner. The left side area is set to have a size so that both corner portions 100 on the left side (lower side) thereof protrude to the outside of the circle 53, and the right side area is set to have a size so that both corner portions 100 on the right side (upper side) thereof protrude to the outside of the circle 53. Further, the corner portions 100 that protrude to the outside are cut, and the excitation electrode 21b for reference and the excitation electrode 21a for detection are respectively formed on the left side area and the right side area inside of the circle 53. The reason why the concave portion 52 of the channel forming member 50 has a circular shape is that, since a circumferential edge of a reaction channel has an arc shape, a liquid flows smoothly without stagnation, which enables to conduct a more accurate measurement.

One end sides of these excitation electrodes 21a, 21b are mutually connected, and a connection portion 27 connecting the electrodes is led out to an outer edge of the quartz-crystal piece 20a and led to the rear surface side. The portion led to the rear surface side serves as a portion to be connected to a later-described conductive path 43b of the wiring board 40 by, for example, a conductive adhesive. Further, a width (size in a longitudinal direction in FIG. 3) of each of these excitation electrodes 21a, 21b is set to have the same size, and the excitation electrodes 21a, 21b are formed in the same size and symmetrically with respect to an extension of a center line passing through a center of the lead-out electrode 28 in a width direction and extending along the lead-out electrode 28.

On the rear surface of the quartz-crystal piece 20a, the excitation electrode 22a for measurement and the excitation electrode 22b for reference are disposed to be separated from each other at positions opposite to the excitation electrodes 21a, 21b, respectively. Further, portions of the excitation electrodes 22a, 22b are led out to the outer edge of the quartz-crystal piece 20a, and the led-out portions are respectively connected to conductive paths 43c, 43a of the wiring board 40. An equivalent thickness of each of the excitation electrodes 21 and the excitation electrodes 22a, 22b is, for example, 0.2 μm, and as an electrode material, gold, silver or the like is used, for example.

On the quartz-crystal piece 20a, an area between the excitation electrode 21b and the excitation electrode 22b forms an oscillation area for reference, and an area between the excitation electrode 21a and the excitation electrode 22a forms an oscillation area for detection. The oscillation area for reference is oscillated by the excitation electrode 21b and the excitation electrode 22b, and the oscillation area for detection is oscillated by the excitation electrode 21a and the excitation electrode 22a.

Figure 3:
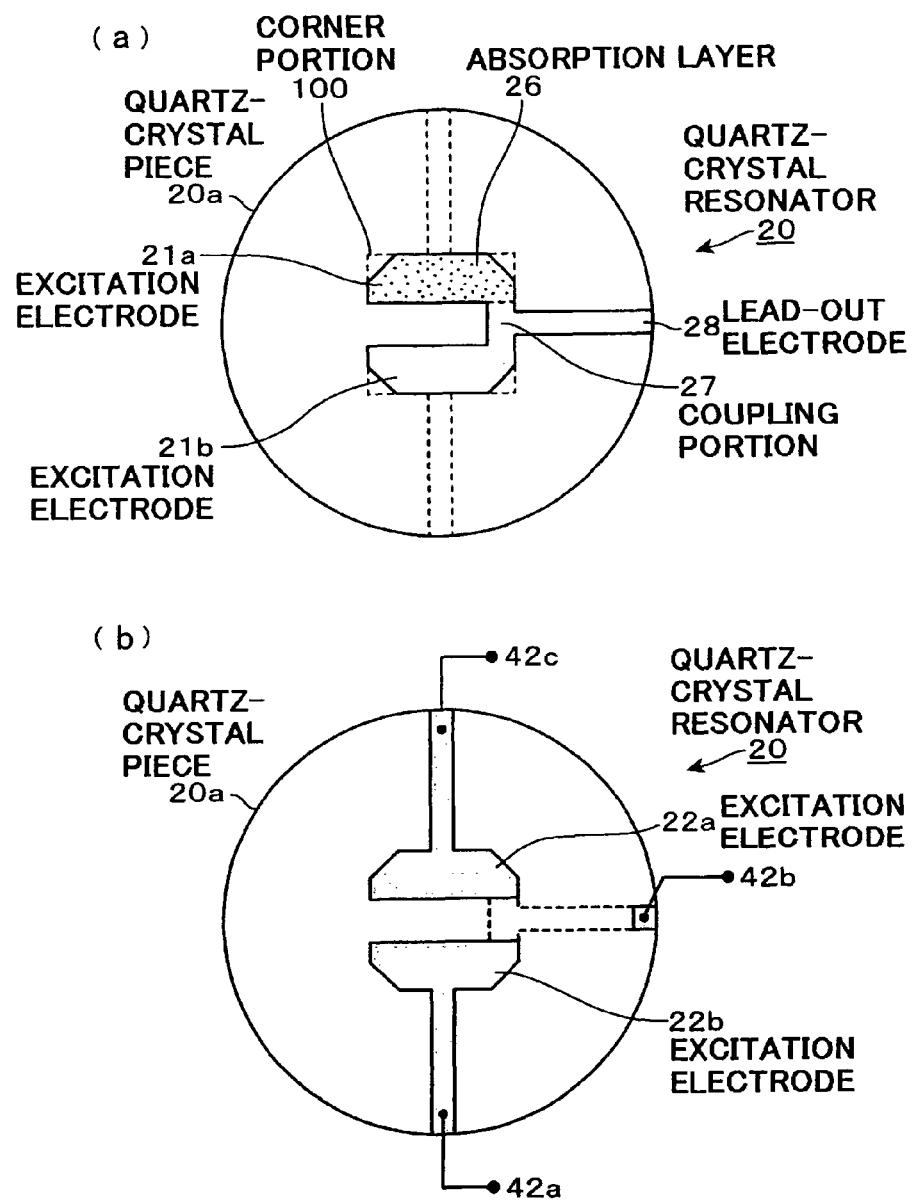
FIGS. 3(a) and 3(b) are a front surface view and a rear surface view showing a quartz-crystal resonator that forms a part a quartz-crystal sensor.

As shown in FIG. 3, an absorption layer 26 is formed on a front surface of the excitation electrode 21a. The absorption layer 26 is formed of an antibody that absorbs a substance to be sensed being an antigen, for example, and absorbs the antigen through an antigen-antibody reaction. Due to a mass load effect caused by the absorption, an oscillation frequency in the oscillation area for detection is lowered. On the other hand, a front surface of the excitation electrode 21b is exposed and the absorption layer 26 is not provided thereon, so that an oscillation frequency corresponding to an influence of disturbance such as a temperature is taken out from the oscillation area for reference. Further, it is also possible to design such that the electrode surface in the area that forms the oscillation area for reference in the excitation electrodes 21 is not exposed and, for instance, a blocking layer formed of, for example, a protein that does not react with the substance to be sensed, is formed thereon.

As shown in FIG. 1, the wiring board 40 is structured by, for example, a printed circuit board, in which a through hole 41 for forming a concave portion that forms an airtight space to which the rear surface side of the quartz-crystal resonator 20 faces, is formed on one end side of the wiring board 40, and holds an outside of the excitation electrodes 22a, 22b. On the other end side of the wiring board 40, terminal portions 42a, 42b and 42c for connecting the wiring board to oscillator circuits are provided. Further, conductive paths 43a, 43b and 43c are formed on the wiring board 40 from the one end side to the other end side thereof, and these conductive paths 43a, 43b, 43c are connected to the terminal portions 42a, 42b and 42c, respectively. Therefore, when the quartz-crystal resonator 20 is placed on the wiring board 40 and the excitation electrodes and the conductive paths are bonded by, for example, a conductive adhesive, the excitation electrodes 21 and the excitation electrodes 22a, 22b are connected to the terminal portions 42b, 42c, 42a via the conductive paths 43b, 43c, 43a, respectively.

Figure 2:
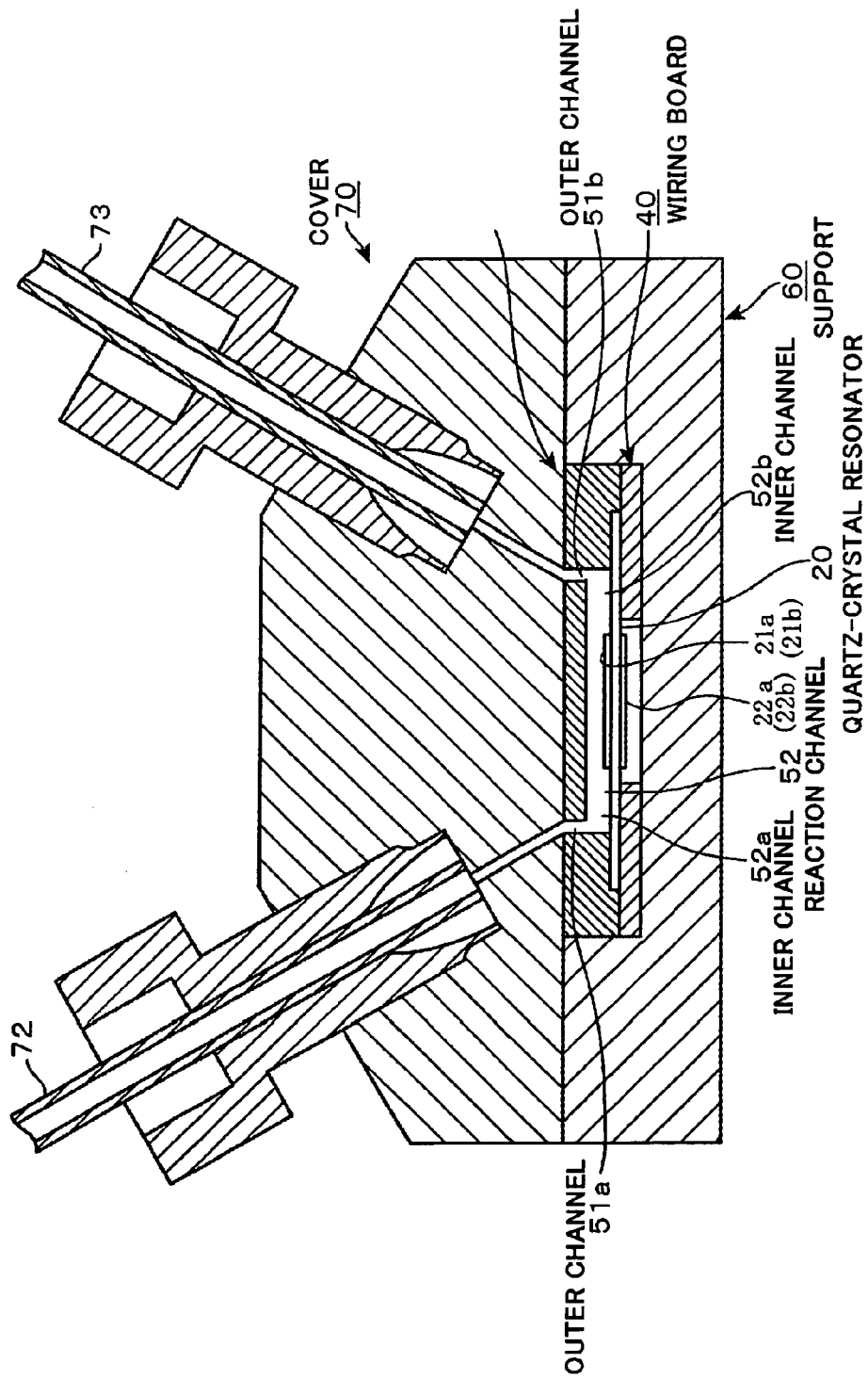
FIG. 2 is a vertical sectional view showing the sensor unit.
Figure 4:
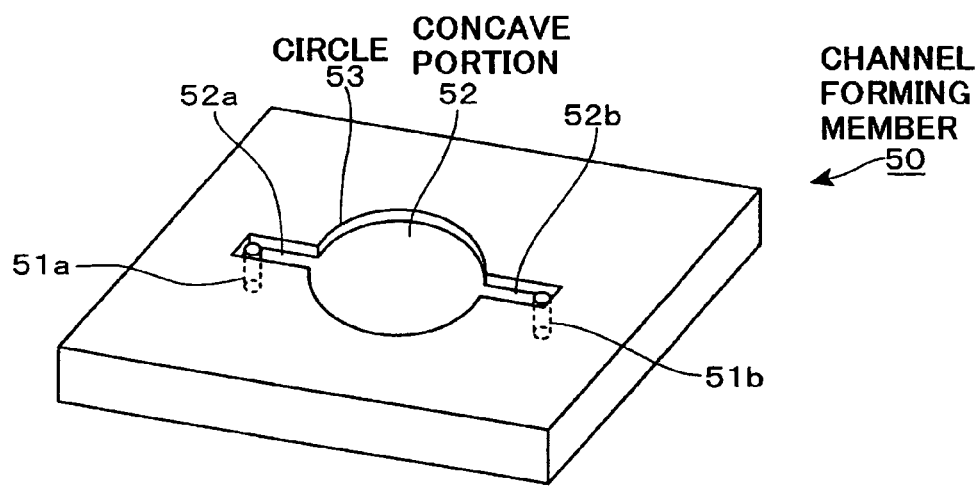
FIG. 4 is a perspective view showing a rear surface of a channel forming member that forms a part of the sensor unit.

Next, the sensor unit 2 will be described using FIG. 2 and FIG. 4. FIG. 2 shows a vertical section of the sensor unit 2. FIG. 4 shows a rear surface side of the channel forming member 50. The channel forming member 50 is formed in a shape corresponding to that on the one end side of the wiring board 40 by using an elastic material, for example, a silicon rubber. A circular concave portion 52 is formed on a center portion on the rear surface side of the channel forming member 50. A diameter of the concave portion 52 is set to be slightly larger than an area of the quartz-crystal resonator 20 including the oscillation area for reference and the oscillation area for detection, and when the channel forming member 50 abuts on the wiring board 40, the oscillation areas are located inside a circular area surrounded by a circumferential edge 53 of the concave portion 52. A height of the concave portion 52 is set to be 0.2 mm or less, for example, and is set to be 0.1 mm in this example.

A ceiling surface of the concave portion 52 is an opposed surface that is opposed to the oscillation areas on the front surface side being one surface side of the quartz-crystal resonator 20 via a gap. In an area between the opposed surface and the quartz-crystal resonator 20, namely, in an area facing the oscillation areas of the quartz-crystal resonator 20, a reaction channel corresponding to a sample fluid supply space is formed. The reaction channel includes an area surrounded by the opposed surface and an inner peripheral surface surrounding a periphery of an upper area of the oscillation areas.

In the channel forming member 50, groove portions 52a, 52b are formed to oppose to each other in a diameter direction of the concave portion 52 across the concave portion 52 and to extend linearly from a circumferential edge of the concave portion 52, as shown in FIG. 4. Accordingly, in a state where the channel forming member 50 and the wiring board 40 are laid one on the other to press the concave portion 52 against the quartz-crystal resonator 20, the concave portion serves as a reaction channel. Note that in the description hereinbelow, both the concave portion and the reaction channel are denoted by a reference numeral 52. Further, the groove portions 52a, 52b form channels surrounded by portions which are not included in the oscillation areas in the quartz-crystal resonator 20 and the channel forming member 50, and are communicated with the concave portion, namely, the reaction channel 52. Note that both the groove portions and the channels are denoted by reference numerals 52a (52b).

Further, in a structure in which the channel forming member 50 and a cover 70 are assembled, there is formed a channel 51a extending vertically upward from an end portion of the inner channel 52a on the opposite side of the reaction channel 52 and further extending diagonally upward, as shown in FIG. 2. The channel 51a corresponds to an outer channel on a supply side, and a liquid supply pipe 72 is connected to an upper end of the outer channel 51a. Further, in the aforementioned structure, there is formed a channel 51b extending vertically upward from an end portion of the inner channel 52b on the opposite side of the reaction channel 52 and further extending diagonally upward. The channel 51b corresponds to an outer channel on a discharge side, and a liquid discharge pipe 73 is connected to an upper end of the outer channel 51b. The inner channel 52a and the outer channel 51a form a liquid supply channel, and the inner channel 52b and the outer channel 51b form a liquid discharge channel.

In a support 60, there is formed a concave portion 61 in which the wiring board 40 and the channel forming member 50 are fit and held. Therefore, by pressing the channel forming member 50 against the wiring board 40 in a state where the wiring board 40 is fit in the concave portion 61, a lower surface of the channel forming member 50 presses the quartz-crystal resonator 20 against the wiring board 40, to thereby fix the quartz-crystal resonator 20. Further, the support 60 is covered from above by the cover 70.

Figure 8:
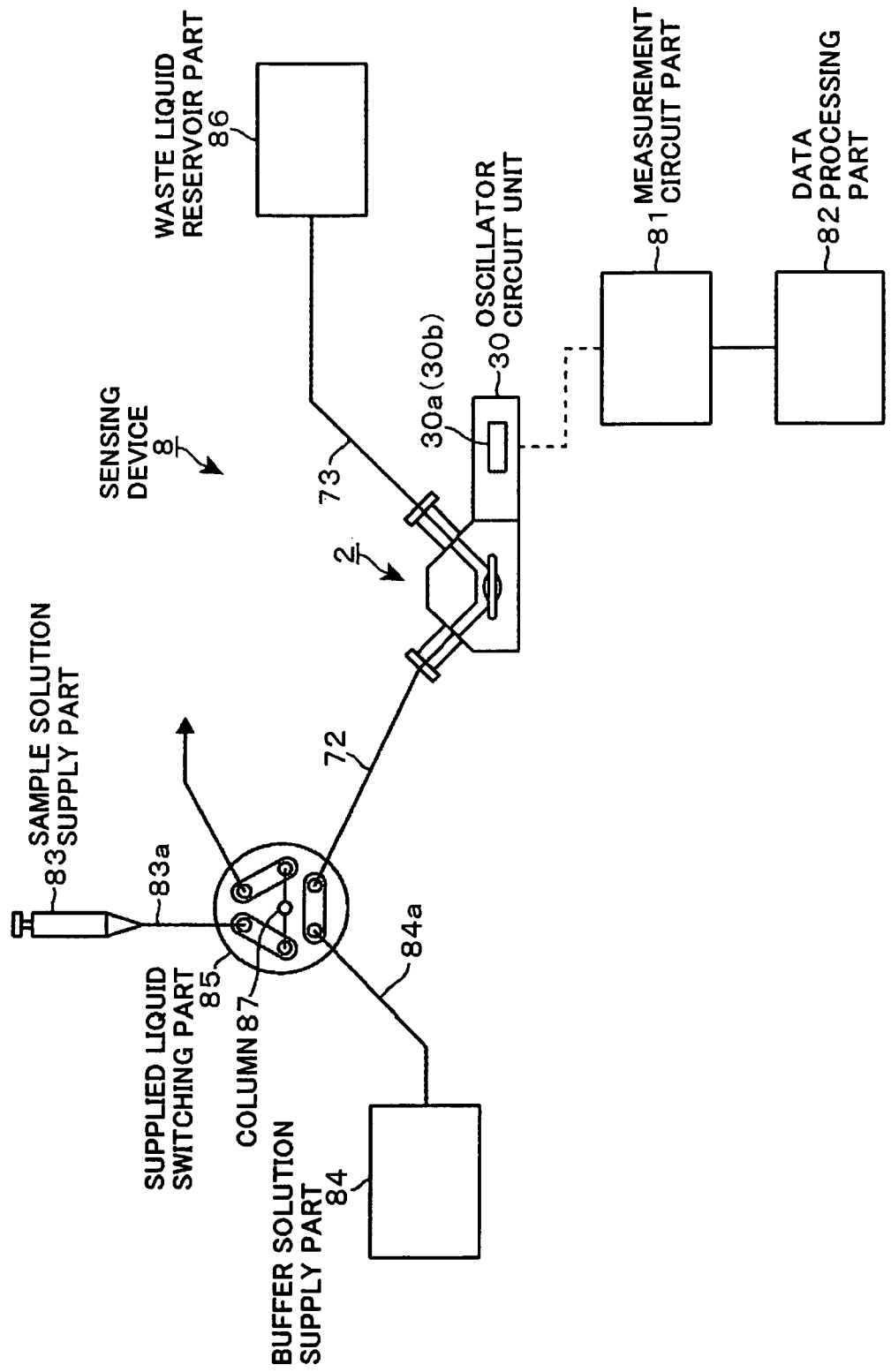
FIG. 8 is a structural diagram showing an entire structure of the sensing device.

Furthermore, as shown in FIG. 8, the sensing device 8 includes an oscillator circuit unit 30, a measurement circuit part 81, a data processing part 82, a sample solution supply part 83, a buffer solution supply part 84, a supplied liquid switching part 85, and a waste liquid reservoir part 86.

Figure 7:
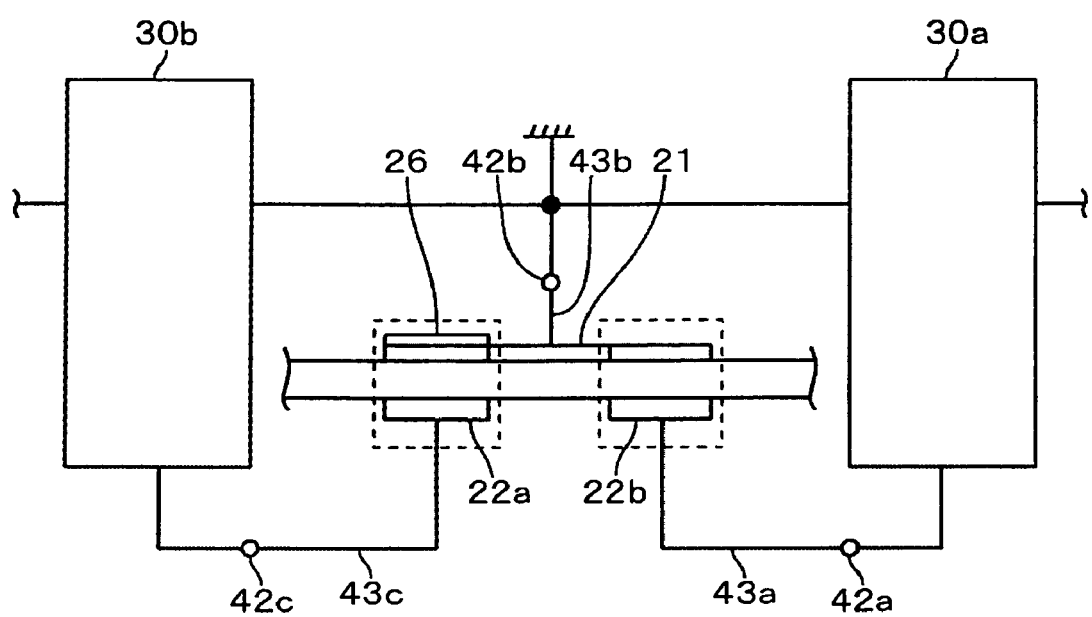
FIG. 7 is a wiring diagram showing a connection between the quartz-crystal resonator and oscillator circuits.

When the oscillator circuit unit 30 is inserted in the sensor unit 2, electrodes 42a, 42b, 42c being connection terminal portions of the wiring board 40 and oscillator circuits 30a, 30b are electrically connected. FIG. 7 is a circuit diagram showing the oscillator circuit unit 30 and the quartz-crystal resonator 20. As shown in this diagram, the oscillation area for reference corresponding to the excitation electrode 22b is connected to the oscillator circuit 30a, and the oscillation area for detection corresponding to the excitation electrode 22*a* is connected to the oscillator circuit 30*b*.

Figure 9:
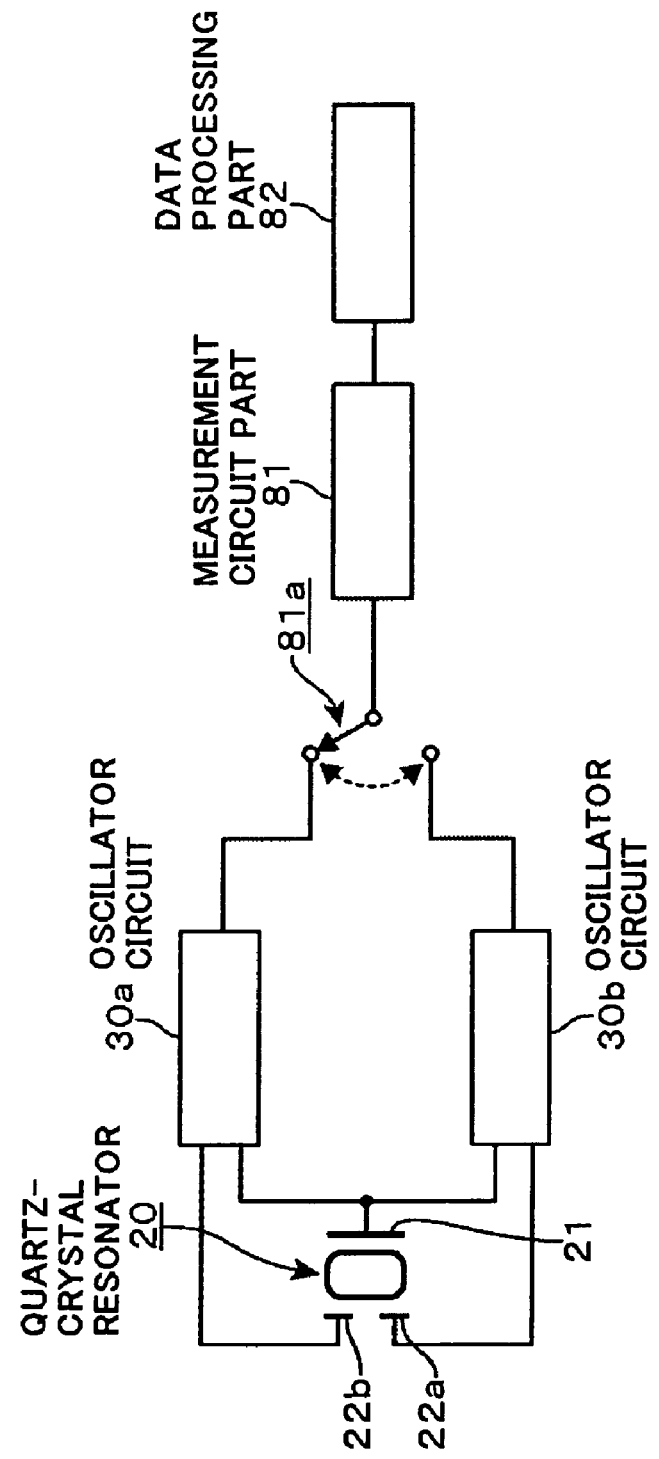
FIG. 9 is a block circuit diagram showing circuits being parts of the sensing device.

On a subsequent stage of the oscillator circuit unit 30, the measurement circuit part 81 and the data processing part 82 are provided, as shown in FIG. 8 and FIG. 9. The measurement circuit part 81 has a function to perform digital processing on a frequency signal being an input signal, for instance, to measure an oscillation frequency. Note that the measurement circuit part 81 may be a frequency counter, and a measuring method thereof can be appropriately selected. Further, on a previous stage of the measurement circuit part 81, there is provided a not-shown switch part 81*a* for taking output signals from the respective oscillator circuits 30*a*, 30*b* in a time-division manner to acquire the resultants. The switch part 81*a* can take the frequency signals from the respective oscillator circuits 30*a*, 30*b* in a time-division manner to acquire the resultants. The data processing part 82 is a part that stores time-series data of the measured frequency and displays the time-series data, and is formed of, for instance, a personal computer.

The sample solution supply part 83 and the buffer solution supply part 84 are connected to the supplied liquid switching part 85 formed of, for example, an injection valve, via pipes 83*a*, 84*a*, respectively. The supplied liquid switching part 85 is connected to the liquid supply pipe 72, and serves to switchably connect either of the pipes 83*a* and 84*a* to the liquid supply pipe 72. The waste liquid reservoir part 86 is connected to the sensor unit 2 via the liquid discharge pipe 73. The supplied liquid switching part 85 switches the channel of liquid in accordance with a signal that is output based on a program in the data processing part 82, for example, but, the switching may also be conducted manually.

Next, the operation of the sensing device 8 structured as above will be described. First, for example, the sensor unit 2 is opened upward, the quartz-crystal sensor 3 is placed on the support 60, and the sensor unit 2 is closed to press a front surface of the quartz-crystal sensor 3 using the channel forming member 50, thereby mounting the quartz-crystal sensor 3 on the sensor unit 2. Next, a buffer solution, for example, a phosphoric acid buffer is supplied to the sensor unit 2 from the buffer solution supply part 84 via the supplied liquid switching part 85. Description will be made regarding the flow of the buffer solution into the sensor unit 2. In the sensor unit 2, the buffer solution passes through the outer channel 51*a* extending diagonally and further extending vertically, to reach an upstream end of the inner channel 52*a*, flows horizontally from the upstream end along the inner channel 52*a*, and flows into the reaction channel 52. Further, the buffer solution flows through the reaction channel 52 toward an entrance of the inner channel 52*b* on the discharge side, flows, after flowing horizontally along the inner channel 52*b*, through the outer channel 51*b* in the upward direction, and is discharged to a not-shown discharge channel.

Meanwhile, the oscillation area for reference and the oscillation area for detection of the quartz-crystal sensor 3 are oscillated by the oscillator circuits 30*a*, 30*b*, respectively, and oscillation frequencies thereof are taken into the measurement circuit part 81 in a time-division manner by the switching of the switch part 81*a*.

Subsequently, after the frequency of the frequency signal obtained by the measurement circuit part 81 is stabilized, the supplied liquid switching part 85 is automatically or manually switched to push out the sample solution, for example, serum or blood already accommodated in a column 87 using the buffer solution, and the sample solution is passed through the reaction channel 52, similar to the buffer solution. At this time, the antigen being the substance to be sensed in the sample solution is absorbed in the absorption layer 26 of the quartz-crystal sensor 3 in accordance with a concentration thereof. Namely, the antigen is captured by the antibody through the antigen-antibody reaction, which results in lowering the oscillation frequency of the oscillation area for detection of the quartz-crystal sensor 3. Therefore, the data processing part 82 obtains a decrement $\Delta f1$ of the frequency in the oscillation area for detection (a difference between the frequency when the buffer solution is flowed and the frequency when the sample solution is flowed). On the other hand, although it is supposed that no variation in frequency occurs in the oscillation area for reference since the absorption layer 26 is not formed on the area, the frequency in the area varies when a disturbance such as a temperature change occurs. If the variation is set as $\Delta f2$, the data processing part 82 subtracts $\Delta f1$ from $\Delta f2$ to cancel the variation in frequency caused by the disturbance, resulting in that the variation in frequency according to an amount of antigen can be determined with high accuracy. Note that the buffer solution is used as a comparison liquid before the sample solution is passed through the reaction channel 52, and as a working liquid pushing out the sample solution in the column 87. However, the comparison liquid and the working liquid are not limited to the buffer solution and may be pure water and the like.

According to the aforementioned embodiment, the corner portions 100, being portions outside of the circle 53, of the strip-shaped excitation electrodes 21*a*, 21*b* formed on a front surface being one surface side of the quartz-crystal piece 20*a* are cut to form the excitation electrodes 21*a*, 21*b*. Therefore, it is possible to enlarge areas of the excitation electrodes 21*a*, 21*b* within an area being surrounded by the circle 53 and including the oscillation areas of the quartz-crystal sensor 3, which contributes to improve the measurement sensitivity.

Figure 12:
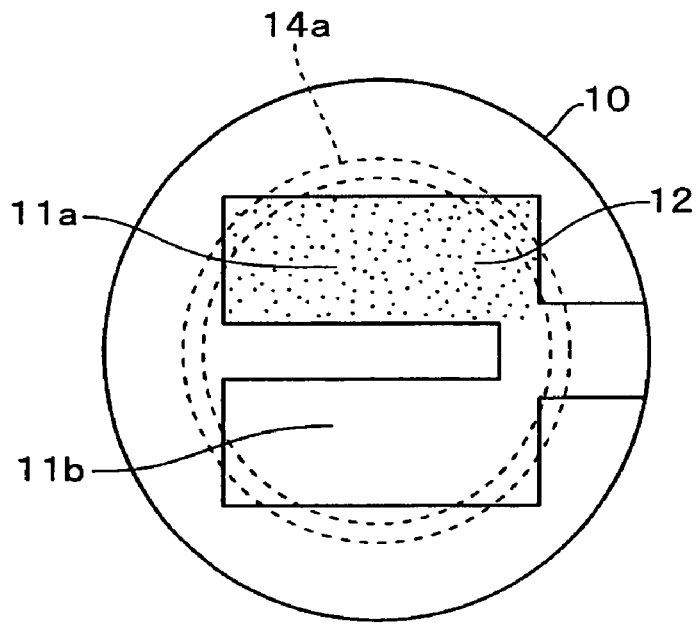
FIGS. 12(a) and 12(b) are top views showing a quartz-crystal resonator as a comparative example.
Figure 12:
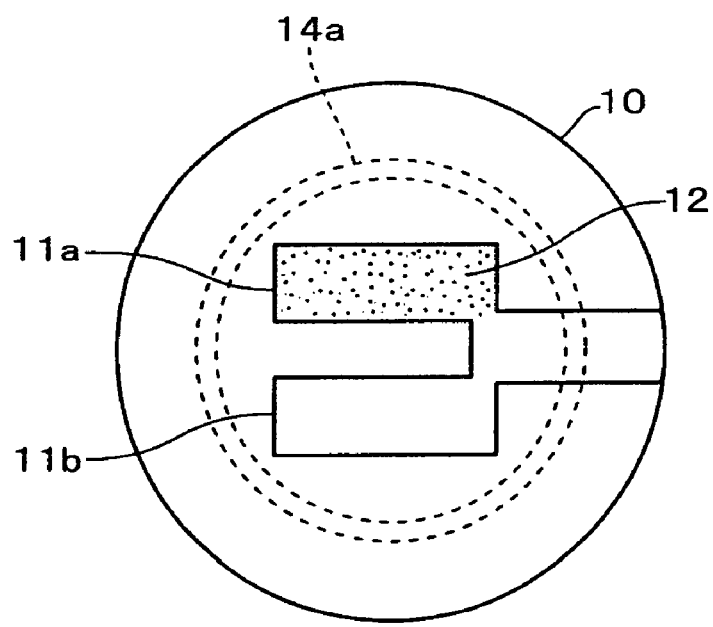

Meanwhile, a disadvantage caused by forming the excitation electrode in a strip shape will be described with reference to FIG. 12. If excitation electrodes 11*a*, 11*b* are designed to be large in size, outer edge portions of the excitation electrodes 11*a*, 11*b* are trodden by an annular pressing portion 14*a* (refer to FIG. 12(*a*)), resulting in that the oscillation becomes unstable. On the other hand, if the excitation electrodes 11*a*, 11*b* are designed to be small in size (refer to FIG. 12(*b*)), the sensitivity of measurement is lowered as described above.

Figure 10:
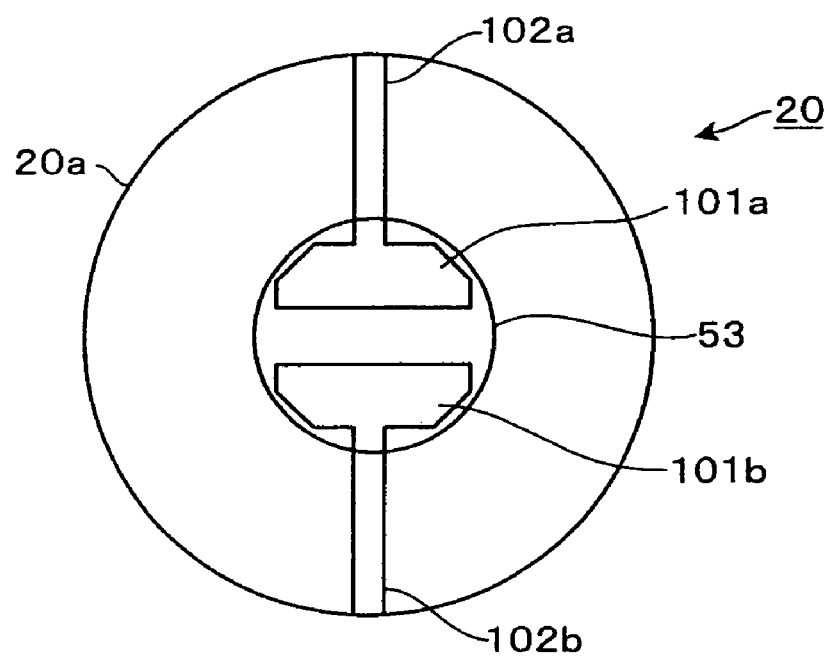
FIG. 10 is a top view showing a quartz-crystal resonator according to an another embodiment.
Figure 11:
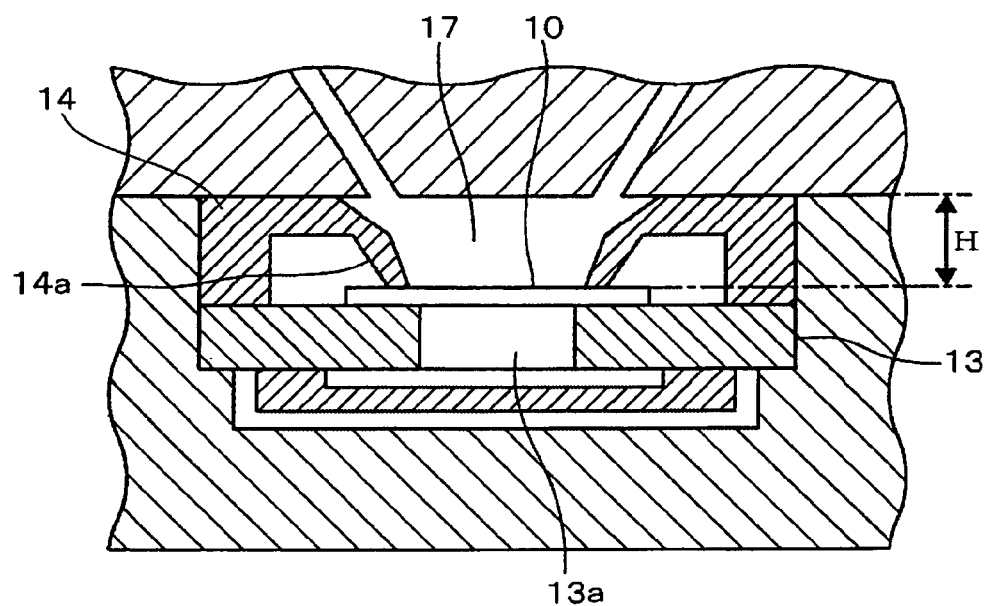
FIG. 11 is a vertical sectional view showing a conventional piezoelectric sensor.

The aforementioned embodiment employs a structure such that, in the two pairs of excitation electrodes provided on the quartz-crystal resonator 20, the excitation electrodes 21*a*, 21*b* on the front surface side are commonly connected to the ground of the oscillator circuit unit 30, and the two excitation electrodes 22*a*, 22*b* on the rear surface side are respectively connected to the oscillator circuits 30*b*, 30*a*, by being separated from each other, but, it is also possible to set the layout of the excitation electrodes on the front surface side and the rear surface side in an opposite manner. FIG. 10 shows such an example, in which excitation electrodes 101*a*, 101*b* which are electrically separated from each other and have a layout corresponding to that of the rear surface side of the quartz-crystal resonator 20 used in the previous embodiment, are provided on a surface, on a side that faces the reaction channel 52, of the quartz-crystal resonator 20. The absorption layer 26 is formed on a front surface of, for instance, the excitation electrode 101*a* that forms the oscillation area for detection. In FIG. 10, 53 corresponds to an outer edge of a circular shape of the reaction channel 52, and corner portions of the excitation electrodes 101*a*, 101*b* are cut so that the electrodes are positioned inside of the circular outer edge 53. Note that when the excitation electrodes 101*a*, 101*b* are formed in a strip shape (quadrangular shape) without cutting the corner portions thereof, they are set to have a size so that the corner portions protrude to the outside of the circular outer edge 53. Lead-out electrodes 102a, 102b are led linearly to the outside from respective center portions of the excitation electrodes 101a, 101b, and end portions of the lead-out electrodes 102a, 102b are connected to the conductive paths 43c, 43a of the wiring board 40. Also in such an example, it is possible to secure wide areas of the excitation electrodes within the circular reaction channel 52, and the same effect can be obtained.

Although the embodiment described above relates to a sensing device of a type in which measurement of frequency is conducted while letting a sample solution flow, the present invention is also applicable to a sensing device of a type in which a piezoelectric sensor is freely attached/detached to a measuring device main body, a liquid storage space is formed in the piezoelectric sensor, and measurement of oscillation frequency of a piezoelectric resonator is conducted in a stationary state by injecting a sample solution and a buffer solution into the space using, for instance, a pipette or the like.

Hereinafter, comparison will be made with respect to areas of electrodes in a quartz-crystal sensor according to the present invention and a conventional quartz-crystal sensor.

[Samples]

As samples, there are used a comparative sample 1 in which an outer edge of excitation electrode is curved (FIG. 13), a comparative sample 2 in which an excitation electrode is formed in a quadrangular shape (FIG. 12(a)), and an example being a quartz-crystal sensor of the present invention. In the comparative sample 1, the comparative sample 2 and the example, a quartz-crystal piece having a diameter of 8.7 mm is used, and a space of 1.5 mm is provided between an electrode for detection and an electrode for reference.

[Area of Electrode]

Figure 13:
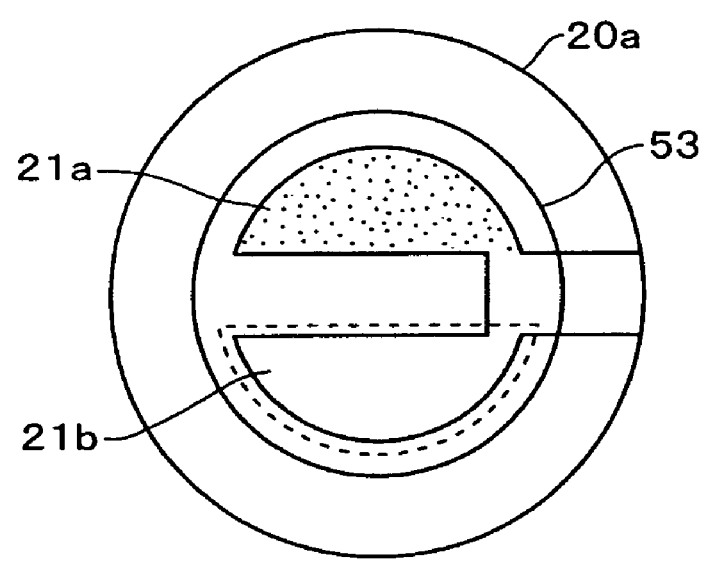
FIG. 13 is a top view showing a quartz-crystal resonator as a comparative example.

In the comparative sample 1, an area of the excitation electrode 21b surrounded by a dotted line portion in FIG. 13 is 6.06 mm$^2$, for example. In the sample 2, an area of the excitation electrode 11b is 8.75 mm$^2$. In the example, an area of the excitation electrode 21b is 7.75 mm$^2$.

[Examination]

As seen from the above, in the comparative sample 1, although the electrodes are not brought into contact with a channel forming member, areas thereof are small (refer to FIG. 13), which results in lowering a measurement sensitivity. Further, in the sample 2, although the excitation electrodes are formed to be large in size, they are trodden by a channel forming member (refer to FIG. 12(a)), so that there is generated a gap between the channel forming member and the quartz-crystal piece, resulting in that a sample fluid is leaked from a reaction channel. However, in the example, it is possible to enlarge the areas of electrodes, which enables to achieve a high measurement sensitivity and creates no problem such that the sample fluid is leaked.

What is claimed is:

1. A sensing device for sensing a substance to be sensed in a sample fluid based on an oscillation frequency of an oscillation area for measurement and an oscillation area for reference, which are formed on a piezoelectric piece, comprising:
   the piezoelectric piece;
   a pair of first excitation electrodes provided on two sides of the piezoelectric piece, so as to form the oscillation area for measurement on the piezoelectric piece;
   a pair of second excitation electrodes provided on the two sides of the piezoelectric piece so as to form the oscillation area for reference, separated from the oscillation area for measurement, on the piezoelectric piece on which the oscillation area for measurement has been formed;
   an absorption layer, which absorbs the substance to be sensed in the sample fluid, and which is formed on one excitation electrode, from among the pair of first excitation electrodes that form the oscillation area for measurement, which is located on one of the two sides of the piezoelectric piece;
   a surrounding member provided, to form a sample fluid supply space common to the oscillation area for measurement and the oscillation area for reference, on one surface side of the piezoelectric piece, to be positioned outside of the first excitation electrodes and the second excitation electrodes, and to surround a first electrode of the pair of first excitation electrodes and a second electrode of the pair of second excitation electrodes in a circular manner; and
   a holding member holding an outside of the oscillation area for measurement and the oscillation area for reference on the other surface side of the piezoelectric piece;
   a first lead out electrode, formed on the piezoelectric piece, for connecting the first electrode of the pair of first excitation electrodes to a conductive path provided on the holding member; and
   a second lead out electrode, formed on the piezoelectric piece, for connecting the second electrode to a conductive path provided on the holding member;
   wherein the first electrode of the pair of second excitation electrodes and the second electrode are formed on one surface side of the piezoelectric piece, in the following shapes:
   a. the first electrode and second electrode are formed symmetrically to be separated from each other into left and right with respect to a center of a circle and being a planar shape contoured to the sample fluid supply space to form strip-shaped left side area and right side area extending in a longitudinal direction in a parallel manner,
   b. each of two corner portions on a left side of the left side area and two corner portions on a right side of the right side area are set to have a size to protrude outside of the circle, and
   c. the corner portions protruding to the outside are cut to make the left side area and the right side area be positioned inside of the circle, and the first electrode and the second electrode are respectively formed on the left side area and the right side area.

2. The sensing device according to claim 1, wherein one end sides of the first and second electrodes provided on the one surface side of the piezoelectric piece are mutually connected by an electrode within the circular sample fluid supply space to provide a common potential to the first and second electrodes, and another electrode of the pair of first excitation electrodes and another electrode of the pair of second excitation electrodes provided on the other surface side of the piezoelectric piece are electrically separated from each other.

3. The sensing device according to claim 1, wherein a supply channel supplying a sample fluid and a discharge channel discharging the sample fluid are connected to the sample fluid supply space, and the measurement of oscillation frequency of a piezoelectric sensor comprising the piezoelectric piece is performed while letting the sample fluid flow into the sample fluid supply space.

* * * * *